(12) United States Patent
Von Drasek et al.

(10) Patent No.: US 9,562,861 B2
(45) Date of Patent: Feb. 7, 2017

(54) METHOD OF MONITORING MACROSTICKIES IN A RECYCLING AND PAPER OR TISSUE MAKING PROCESS INVOLVING RECYCLED PULP

(75) Inventors: William A. Von Drasek, Oak Forest, IL (US); Brett Brotherson, Lisle, IL (US); Sergey M. Shevchenko, Aurora, IL (US); Michael J. Murcia, DeKalb, IL (US)

(73) Assignee: Nalco Company, Naperville, IL (US)

( * ) Notice: Subject to any disclaimer, the term of this patent is extended or adjusted under 35 U.S.C. 154(b) by 478 days.

(21) Appl. No.: 13/079,891

(22) Filed: Apr. 5, 2011

(65) Prior Publication Data

US 2012/0258547 A1    Oct. 11, 2012

(51) Int. Cl.
*G01N 21/76* (2006.01)
*G01N 21/64* (2006.01)
(Continued)

(52) U.S. Cl.
CPC ........ *G01N 21/6486* (2013.01); *G01N 21/643* (2013.01); *G01N 21/6458* (2013.01); *G01N 21/85* (2013.01); *G01N 33/343* (2013.01)

(58) Field of Classification Search
CPC .............. G01N 21/643; G01N 21/6458; G01N 21/6486; G01N 21/85; G01N 33/343
See application file for complete search history.

(56) References Cited

U.S. PATENT DOCUMENTS 3,728,032 A * 4/1973 Noll .................. G01N 21/05
250/435

7,537,732 B2 * 5/2009 Gustafson et al. ........ 422/82.05
(Continued)

FOREIGN PATENT DOCUMENTS

JP    2007332467    12/2007
JP    2010-520444 A    6/2010
(Continued)

OTHER PUBLICATIONS

Blanco et al.; Overview of two major deposit problems in recycling: slime and stickies, Part II, Stickies problems in recycling; Progress in Paper Recycling (2002), 11(2) 26-37.
(Continued)

*Primary Examiner* — Robert Xu
(74) *Attorney, Agent, or Firm* — Leydig, Voit & Mayer, Ltd.

(57) ABSTRACT

A challenge in using recycled material in the papermaking process is the presence of hydrophobic organics with adhesive properties commonly known as "stickies." Hydrophobic agglomerates can result in spots or defects in the final paper product or deposit on papermaking equipment resulting in poor runnability and downtime. Technologies for monitoring and controlling microstickies exist. However, a need exists for a technique to rapidly determine the size and content of macrostickies (diameter>100 microns) in recycled pulp process streams. The present invention is a device and method to perform real-time macrostickies and/or any visible hydrophobic particle analysis in an aqueous medium. Using the present invention, furnish quality can be monitored and treatment performance can be monitored and controlled. The technique is based on fluorescence image analysis to identify and count sticky particles as well as measure their size.

21 Claims, 7 Drawing Sheets

(51) Int. Cl.
*G01N 21/85* (2006.01)
*G01N 33/34* (2006.01)

(56) References Cited

U.S. PATENT DOCUMENTS

| | | | |
|---|---|---|---|
| 7,909,963 | B2 | 3/2011 | De Cesare |
| 2003/0070927 | A1 | 4/2003 | Merchant et al. |
| 2006/0281191 | A1 | 12/2006 | Duggirala et al. |
| 2008/0308241 | A1* | 12/2008 | Di Cesare ............ 162/162 |
| 2009/0056897 | A1 | 3/2009 | Shevchenko et al. |
| 2009/0084510 | A1 | 4/2009 | Perry et al. |
| 2009/0260767 | A1 | 10/2009 | Gerli et al. |
| 2010/0012284 | A1 | 1/2010 | Kaub |
| 2010/0236732 | A1 | 9/2010 | Gerli et al. |

FOREIGN PATENT DOCUMENTS

| | | |
|---|---|---|
| JP | 2010-529421 A | 8/2010 |
| WO | WO 2009/100028 A1 | 8/2009 |
| WO | 2010007390 A3 | 1/2010 |

OTHER PUBLICATIONS

Blanco et al.; Full characterization of stickies in a newsprint mill: the need for a complementary approach; TAPPI Journal (2007), 6(1) 19-25.

Cao et al.; Recycled paperboard mill macrostickie study; Preparation for the Seventh Research Forum on Recycling, Quebec City, Quebec, Canada (2004) 149-58.

Delagoute et al.; Stickies related deposits in papermaking drying section: origin and recycling process influence; Proc. 57th Annual Congr. ATIP; Grenoble, France (2004).

Delagoute; Management and control of stickies; Progress in Paper Recycling (2005), 15(1) 31-41.

Doshi; A review of stickies measurement methods; Progress in Paper Recycling (2009), 18(3) 20-30.

Doshi et al.; Comparison of macrostickies measurement methods; TAPPI EPE Conference—Stickies Workshop, Memphis, TN (2009), 12-21.

Doshi et al., eds.; Management and control of stickies, In: Paper Recycling Challenge, Doshi & Associates (1998) vol. III, 195-233.

Doshi et al.; Review of quantification methods for PSA and other stickies; TAPPI Recycling Symposium (2000) 701-11.

Gabl et al.; Methods used for the measurement of primary and secondary stickies—macro, micro, and disco stickies; Paper Technology (2006), 47(6) 35-40.

Hong et al.; Hydrophobic aminostyryl quinolinium dyes as new fluorescent stains for proteins in sodium dodecyl sulfate—polyacrylamide gel; Bulletin of the Korean Chemical Society (2004), 25(3) 345-46.

Oliveira et al.; Solvatochromic fluorescent probes in bicontinuous microemulsions; Journal of Molecular Structures (2001), 443-47, 563-64.

Putz; Stickies in recycled fiber pulp; Papermaking Science and Technology (2000), 7, 441-504.

Sithole et al.; Assessment of methods for the measurement of macrostickies in recycled pulps; Progress in Paper Recycling (2008), 17(2) 16-25.

Vahasalo et al.; Influence of latex properties on the formation of white pitch; TAPPI Journal (2005), 4(5) 27-31.

Wang et al.; Recent developments of an in-situ image detecting system for floc characterization and monitoring; Water Science and Technology (2010), 61(11) 2699-2706.

* cited by examiner

METHOD OF MONITORING MACROSTICKIES IN A RECYCLING AND PAPER OR TISSUE MAKING PROCESS INVOLVING RECYCLED PULP

FIELD OF THE INVENTION

The invention relates to a method that measures the concentration and size of visible hydrophobic particles ("macrostickies") in flowing pulp slurries. More specifically, the invention relates to a device and method that performs real-time macrostickies analysis in a flowing pulp stream. The method uses fluorescence image analysis to identify and count macrostickies as well as measure their size.

BACKGROUND

Characterization of visible hydrophobic particles, more particularly visible hydrophobic particles in aqueous media is an important general problem, with a specific application in the pulp and paper industry, especially when dealing with secondary fiber. Deposition of stickies and tackies and formation of large agglomerates of hydrophobic materials are major obstacles in the manufacture of paper and tissue using recycled fiber. For paper grades, these non-polar, tacky contaminants, particularly when liberated during repulping, can become both undesirable components of papermaking furnishes and troublesome deposits on the mill equipment; for example, wires of the paper or tissue machine.

Stickies and tackies are organic materials that do not have a precise definition. Stickies and tackies are tacky substances contained in the pulp and process water system that deposit on paper/tissue machine clothing, cylinders, or rolls. Synthetic materials constituting stickies or tackies (a.k.a. white pitch) include adhesives and coating binders such as styrene butadiene rubber, ethylene vinyl acetate, polyvinyl acetate, polyvinyl acrylate, polyvinyl butyral, polybutadiene, etc., and components of printing ink such as wax, alkyd resins, polyol acrylates, etc. Natural wood pitch normally present in virgin pulp consists of fatty acids, fatty esters and rosin acids. Natural wood pitch is more polar than stickies, but, generally, also belongs to the class of hydrophobic admixtures and is similar in its properties relevant to contaminant monitoring.

The most common classification system of stickies used by the pulp and paper industry is based on size to categorize stickies into three classes: macro, micro and colloidal. Macrostickies are considered to be particles that result from primary disintegration of the recycled material during repulping. For classification purposes, macrostickies typically have a particle size greater than 0.1 mm. Macrostickies can be removed largely by coarse and fine screening.

Macrostickies are also those stickies that remain as screening residue after laboratory screening having a slot width of 0.10-0.15 mm. Major sources of these materials are hot melts and pressure-sensitive adhesives. Macrostickies can include adhesives and coating binders such as styrene butadiene rubber, ethylene vinyl acetate, polyvinyl acetate, polyvinyl acrylate, polyvinyl butyral, polybutadiene, and/or components of printing ink such as wax, alkyd resins, polyol acrylates, and other like substances. The methods of quantification of macrostickies that are currently practiced are laborious, and no continuous monitoring technique exists.

Micro (0.1-0.001 mm) and colloidal (<0.001 min) stickies are those that can pass the screening slots. The microstickies that pass the screens can later agglomerate and lead to deposits on the paper/tissue machine or pass into the product as newly formed secondary macrostickies.

This differentiation, based on size, is arbitrary and cannot be strictly applied to different monitoring methods. Thus, the size limitation of the proposed method is not the same as size limitations defining macrostickies, while those having skill in the art will recognize the method as one for macrostickies monitoring. In fact, in pulp and paper applications, the size of measured stickies can be smaller than 0.1 mm provided that the particles are detectable through an imaging system that may include a digital microscopic camera and optically differentiated from the surrounding medium. Colloidal stickies do not fit this definition, while a 0.05-0.10 mm fraction of macrostickies in fact does fit this definition. The size limits are generally defined by the capabilities of the imaging system used and the signal to noise ratio of the captured image, where the noise can be electronic as well as background from the surrounding medium.

Nalco has developed proprietary technology for monitoring microstickies based on quartz crystal microbalance (QCM) (see, e.g., Duggirala & Shevchenko, U.S. Patent Application Publication No. 2006/0281191; Shevchenko et al., U.S. Pat. No. 7,842,165). The QCM-based technology is suitable for microstickies but not macrostickies monitoring because the latter cannot be expected to stick to the QCM surface in the flow of the pulp slurry.

It is known that fluorescent dye molecules that emit from an intramolecular charge transfer state are sensitive to medium polarity. The dye molecules' fluorescence (both wavelength and intensity) is affected by the polarity as well in the case of non-homogeneous systems, such as suspensions of non-soluble organic liquids in water. These dyes can bind directly to hydrophobic particles or droplets that have a similar effect on the dyes' optical properties. Based on these properties, methods were developed to visualize protein stains based on dyes that bind non-covalently to protein complexes. These techniques have also been coupled with electrophoresis procedures.

Perfect et al. (WIPO Patent Application Publication No. WO2010007390) describes a method to assess multiphase (water/organic) fluid compositions that specifically monitor oil in water in the area of wastewater treatment. Perfect et al. identified Nile Red as a preferable molecule used to perform the method. Nile Red is ideal for assessment of the organic phase of a multiphase sample because it emits a more intense signal on contact with the organic phase than on contact with the aqueous phase, the shift in wavelength being significant. Nile Red has strong photochemical stability, an intense fluorescence emission peak, and relatively low cost. Perfect et al. further discloses that the method can be used to determine the size distribution of droplets of either the organic phase or the aqueous phase in the multiphase sample based on the image analysis. Perfect et al. further anticipates at-line and on-line applications.

Gerli et al. (U.S. Patent Application Publication No. 2009/0260767) describes a method of monitoring and controlling one or more types of hydrophobic contaminants in a papermaking process. The method utilizes the measurement with dyes, which are capable of fluorescing and interacting with the hydrophobic contaminants. Gerli et al. does not allow for the measurement of macrostickies or on-line monitoring. Gerli et al. provides for bulk characterization of a summary microstickies in a sample of filtered material.

Sakai (Japanese Patent Application Publication No. 2007/332467) proposed microscopic image processing of particles in a deinked pulp slurry for quantification of the particles. However, the process described in Sakai does not relate to the continuous monitoring with dye injection.

Accordingly, there is a need for complementing microstickies measurement technology with a comparable on-line method for macrostickies monitoring. Such a measurement method would allow a papermaker/recycler to use lesser quality furnish and more recycled pulp than is currently able to be used. Desirably, the two measurement methods would allow for continuous on-line process adjustments in order to maximize process efficiency.

SUMMARY OF THE INVENTION

The present invention is directed toward a method for monitoring a variable in an aqueous pulp slurry. The aqueous slurry is comprised of contaminants. The method comprises the steps of providing a flow of the aqueous slurry; shining light into the aqueous pulp slurry; adding a hydrophobic dye into the aqueous pulp slurry, the adding performed at conditions causing the hydrophobic dye to interact with the contaminants, the interaction causing a change in fluorescent emission; capturing an image of the change in fluorescent emission; altering the image to isolate the change in fluorescent emission caused by the interaction of the hydrophobic dye with at least one contaminant of the contaminants; and measuring the variable of the aqueous pulp slurry based on the altered image.

The present invention is also directed toward an apparatus for monitoring a variable of an aqueous pulp slurry, the aqueous pulp slurry comprised of contaminants. The apparatus comprises a container equipped with a mixer, a temperature control device, a sample cell, an aqueous pulp slurry circulation device, a light source, an imaging device, and a processing device. The temperature control device is operably attached to the apparatus to control the temperature of the aqueous pulp slurry. The container is operably attached to the sample cell and the aqueous pulp slurry circulation device so that the aqueous pulp slurry circulates through the sample cell. The light source is operably positioned so that it delivers light into the aqueous pulp slurry as the slurry passes through the sample cell. The imaging device is operably positioned to capture an image of a change in fluorescent emission. The sample cell is equipped so as to operably recycle the aqueous pulp slurry into the container.

The methods are all preferably used for the characterization of macrostickies in an aqueous medium. These and other features and advantages of the present invention will be apparent from the following detailed description, in conjunction with the appended claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description of the Invention," relates to a requirement of the United States Patent Office, and does not imply, nor should be inferred to limit the subject matter disclosed herein.

DEFINITIONS

For purposes of this patent application, the following terms have the definitions set forth below:

"Aqueous pulp slurry" means any aqueous medium that may or may not contain some level of pulp.

"Aqueous pulp slurry circulation device" means a device that circulates an aqueous pulp slurry through a conduit. A typical aqueous pulp slurry circulation device is a pump.

"Capturing" means recording an image.

"Concentration" means any measurement of a subset of a whole per the whole. Concentration as related to this application may be measured as mass of the subset per volume of the whole, volume of the subset per volume of the whole, quantity of the subset per mass of the whole, quantity of the subset per volume of the whole, quantity of the subset per quantity of the whole, and so forth. For the purposes of this patent application, particle count is a type of concentration measurement.

"Contaminant" means any organic material found in an aqueous slurry that is not pulp, water, or a material that is intentionally added to the aqueous slurry. Typical contaminants are stickies, pitch, and like substances.

"Digital microscopic camera" means a camera that is capable of capturing microscopic images in a digital storage format.

"Flow-through cell" means an apparatus having at least one non-opaque space that allows flow of a fluid, slurry, or the like, through the apparatus, allowing for outside observation of the flow through the apparatus.

"Fluid" includes any aqueous medium, homogeneous or heterogeneous, and, in particular, liquids used in the pulp and paper industry such as an aqueous papermaking suspension from a papermaking process (e.g., a fluid containing fibers in a pulping stage), a thin stock, a thick stock, aqueous suspensions drawn from the papermaking process (e.g., various locations from a papermaking machine or pulping process), aqueous fluid in a Uhle box, press dewatering section, and/or any part of the papermaking process that one of ordinary skill in the art would need to monitor hydrophobic contaminants. For purposes of this patent application, a slurry is a fluid.

"Hydrophobic dye" means any dye capable of emitting a fluorescent emission when interacting with a contaminant as defined above.

"Macroscopic contaminant" means any contaminant having a particle size of greater than or equal to 0.10 mm, as typically used by the pulp and paper industry. A visible hydrophobic particle is an example of a type of macroscopic contaminant, though it may not be the only type of macroscopic contaminant.

"Non-macroscopic contaminant" means any contaminant that is not a macroscopic contaminant.

"Papermaking process" means a method of making any kind of paper product (e.g., paper, tissue, board, etc.) from pulp comprising forming an aqueous cellulosic papermaking furnish, draining the furnish to form a sheet, and drying the sheet. The steps of forming the papermaking furnish, draining, and drying may be carried out in any manner generally known to those skilled in the art. The papermaking process may include a pulping stage (e.g., making pulp from woody raw material or secondary fiber) and bleaching stage (e.g., chemical treatment of the pulp for brightness improvement). Furnishes can contain fillers and/or other contaminants.

"Temperature control device" means any device or combination of devices that provide heating, cooling, or heating and cooling, either manually or automatically, so that a temperature may be controlled.

"Variable" means a measurable or quantifiable value. While not wishing to be restricted, examples of variables typically measured in the context of the invention include particle size distribution, concentration, particle count, the effectiveness of an additive, etc.

"Visible contaminant" means any contaminant that is detectable by a microscope or microscopic camera. A visible contaminant is a form of macroscopic contaminant.

The invention is directed to an on-line method for assessing visible, and more specifically macroscopic contaminants in an aqueous slurry, particularly an aqueous pulp slurry containing recycled furnish. These contaminants can be broadly divided into two categories: hydrophilic dirt particles and hydrophobic stickies. Hard hydrophobic particles such as pieces of plastic can also be present in such a slurry, but these particles are typically removed at a pulp preparation stage of a papermaking process. The method allows quantifying said contaminants in a flow of dilute pulp slurry. Specifically, intermediately sized stickies and macrostickies can be selected and characterized on-line. In its preferred embodiment, the method involves treatment of the pulp slurry with a fluorescent dye. Both concentration and size distribution of these particles can be assessed through combined hydrophobicity-dependent fluorescent dye injection, optical excitation and imaging, and image analysis. In addition, visible dirt particles can be characterized using conventional optical means. Thus, the full picture of macroscopic contamination of recycled pulp can be obtained using the same optical flow-through setup that can be realized in the form of a pump-driven, closed-loop, batch configuration or a continuous sidestream apparatus at a mill.

It is important that this characterization can be made in an actual pulp flow, with furnish present, without any filtering or sample preparation. Moreover, the pulp can be characterized in the same experiment for the level of hydrophobic microparticles deposited on its surface. Altogether, the method allows one to characterize the efficiency of screening at the mill, the quality of the supplied furnish, and the degree of hydrophobic coating of the pulp.

As a first aspect of the current invention, a method and apparatus are described for detecting visible stickies in a multiphase fluid made up of water having a chemical composition typically found in a paper mill, fibrous pulp, and mixture of hydrophilic and hydrophobic particles. Detection of the visible hydrophobic particle by fluorescence requires at least four steps.

First, a fluorophore dye is added into a multiphase flow at a fixed concentration, mixing rate, time, and sample temperature. In a closed-loop system, the dye is dosed into a container that contains the bulk of the pulp slurry and that is equipped with a mixer. The pulp is circulated through the loop, residence time is determined experimentally (until the readings are stable), and measurements are taken repeatedly to assess the margin of error. In a sidestream flow-through system, the mixing is provided by devices, potentially including a stationary mixer or a coiled hose and sufficient residence time. Controlling residence time, concentration, and sample temperature affects the fluorophore dye absorption rate on to the hydrophobic particle surface, thereby affecting the measurement time.

Second, an excitation light source illuminates the hydrophobic particle having a fluorophore dye sorbed on the surface.

Third, an imaging device is used to measure fluorescence emitted from the hydrophobic particle resulting from the energy transfer process of the fluorophore absorbing photons from the excitation source.

Fourth, an imaging processing algorithm is used to distinguish a hydrophobic particle from the background and determine the size of the particle. By collecting and processing a series of images in a flowing system the number and particle size distribution for macrostickies is determined. Details for the different steps are further described.

Figure 1A:
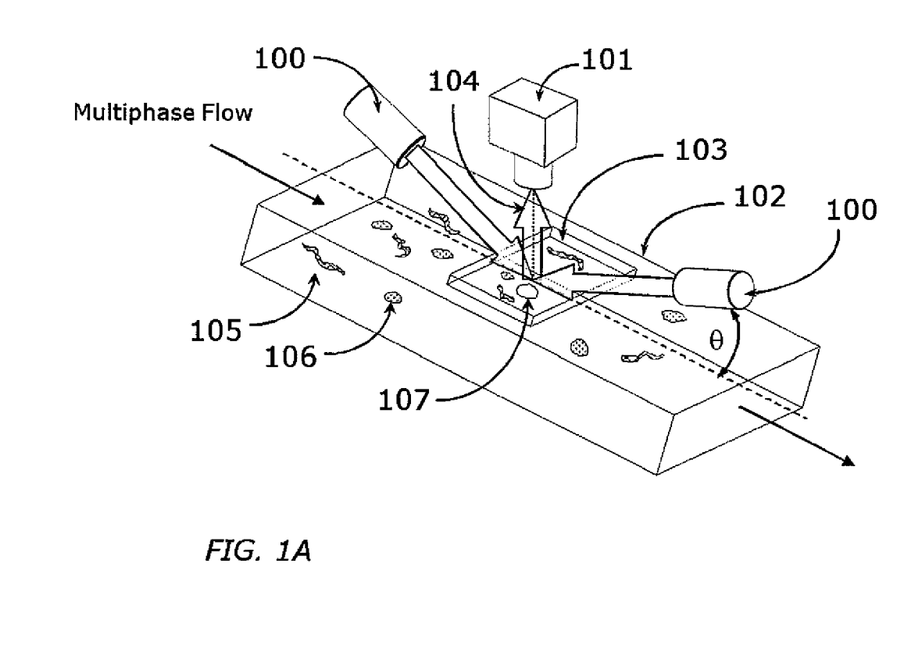
FIG. 1A is a perspective view of a first embodiment of the invention.

An apparatus to detect and measure the size and distribution of macrostickies is illustrated in FIG. 1A. The apparatus consists of a flow cell 102 with optical access 103 and an imaging device 101. The multiphase fluid made up of fibrous material 104 and particles 105 that can be either hydrophobic or hydrophilic flows through the cell past the optical access window 103. A light source 100 operating at the excitation wavelength for the hydrophobic dye (Nile red) is directed to the optical access window 103. Detection of the hydrophobic particle(s) is made with an imaging device 101 by monitoring the fluorescence light emission 106. The emitted light is at lower energy (longer wavelength) compared to the excitation source, thus allowing the hydrophobic particles to be distinguished from the excitation source wavelength and the emission wavelengths by using narrow-band or bandpass filters.

The excitation source 100 used can be either pulsed or continuous. Examples of light sources that can be used include wavelength specific sources such as LED, laser (diode, Nd:YAG, Ar-ion, etc.), or combination of any white light source (LED, incandescent, arc lamp, etc.) and optical filter to attain the appropriate excitation wavelength(s). The preferred method is to collimate the light source to uniformly illuminate the area being imaged. Multiple or a single light source can be used with an angle of incidents (θ) ranging from slightly greater than zero degrees to perpendicular. For the configuration shown in FIG. 1A, the detection and position of the excitation light is made on the same side of the optical access window 103. In this configuration, excitation light losses from scatter and extinction in the multiphase fluid are minimized because the light propagation length through the medium is minimized. Alternative configurations for introducing the excitation light are shown in FIGS. 1C and 1D.

A preferred embodiment of imaging device 101 is an array detector camera with a combination lens and filter assembly. The camera detector can be either a CMOS or CCD type provided the quantum efficiency (or low lux) is high enough at short exposure times to detect the fluorescence. The combination of high quantum efficiency and short exposure time is required to detect the particles' weak fluorescence in a flowing medium without skewing or blurring. The typical quantum efficiency for standard commercially available CCD cameras is high enough to detect fluorescence for this application. In addition, typical CCD cameras use global shuttering that helps in reducing image skewing or blurring.

CMOS cameras can also be used, but greater care in camera selection is needed because these cameras typically have poorer quantum efficiency and use a rolling shutter technology. Specialized high gain CMOS or image intensified CMOS cameras can be used, but these devices are typically more expensive. For the lens filter combination, the choice of lens depends on the desired magnification and the filter used will depend on the fluorescence emission wavelength.

Figure 1B:
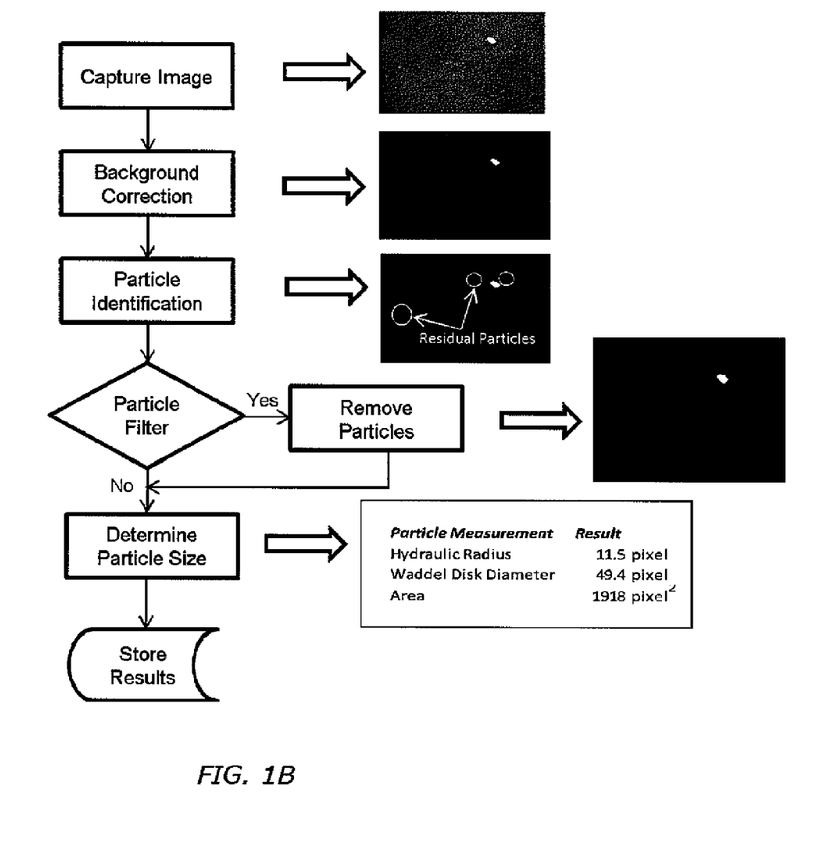
FIG. 1B is a flow chart of several of the steps used to determine particle size of a macrosticky in multiphase flow.
Figure 1C:
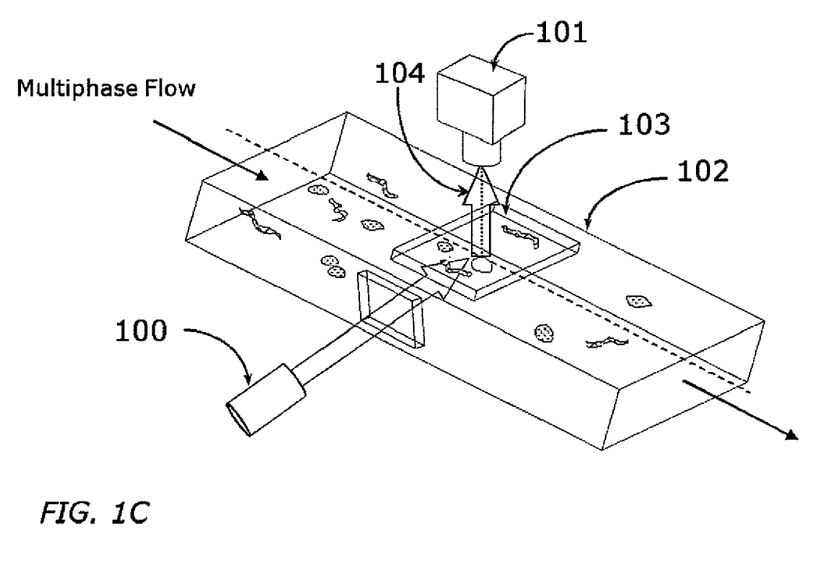
FIG. 1C is a perspective view of a second embodiment of the invention.
Figure 1D:
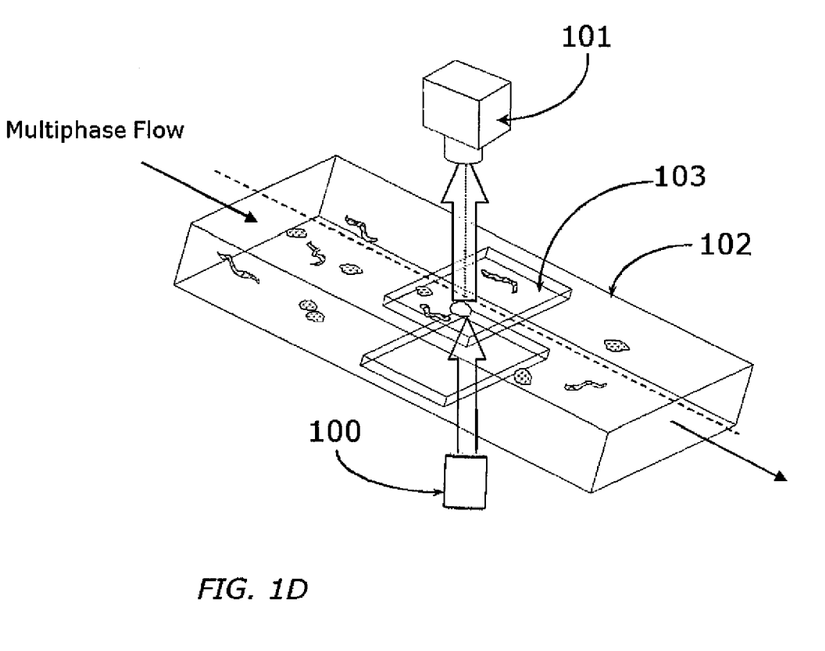
FIG. 1D is a perspective view of a third embodiment of the invention.

The image processing steps used in the identification and size determination of a hydrophobic particle are outlined in the flow chart shown in FIG. 1B. Image processing can be made in real-time by capturing an image and processing the image with either a computer or a processor that is integrated with or embedded into the camera. Alternatively, images can be collected using a storage medium (e.g., magnetic tape, hard drive, etc.) for post-processing at a later time.

The flow chart in FIG. 1B lists the processing steps and sample image to illustrate the effect of each processing step. In the first step, a raw image is captured for analysis. The sample image shown is from laboratory measurements of a mill flowing sample using a configuration similar to that illustrated in FIG. 1A. In this example, a hydrophobic particle is clearly identified by the bright spot in the image. However, the raw image also shows smaller particles along with fibrous material with an overall image background that appears gray. By applying background correction, in this case a power transformation is applied to decrease the brightness and contrast in dark regions while increasing the contrast in bright regions. As seen in the sample image, the transformation essentially removes the gray background along with a large portion of background emitting features. Alternative background correction methods may include subtracting an image collected with no change in fluorescence caused by hydrophobic contaminants or subtracting an average of previous images. For image averaging, a running average can be used with an algorithm to identify and remove images from the average that contain fluorescing hydrophobic contaminants. Particle identification is made in the next step by converting the image to binary with a threshold limit to further remove weak emitting features in the image. In this example, some small residual particles remain in the binary image for a fixed threshold setting as indicated on the image. Additional filtering based on a size parameter (e.g., particles smaller than a specified size) removes the images of the small residual particles resulting in a clean binary image with a single particle. In the final step, particles are characterized by measurements related to their attributes, such as particle area, hydraulic radius, Waddel disk diameter, location, vertical height, horizontal length, etc., reported in terms of pixel number. Converting from pixel values to physical units (e.g., mm per pixel) is accomplished by one skilled in the art by calibrating the camera using a known standard. Results from the single frame analysis are then stored and the process is repeated for the next captured image. By collecting analysis results for n images, one can develop frequency distributions and descriptive statistics of the different particle attributes. Historical trending of the particle attributes (e.g., mean particle size) can be performed to track the characteristics of the fluid and the impact of process operational and chemical treatment changes.

Figure 1E:
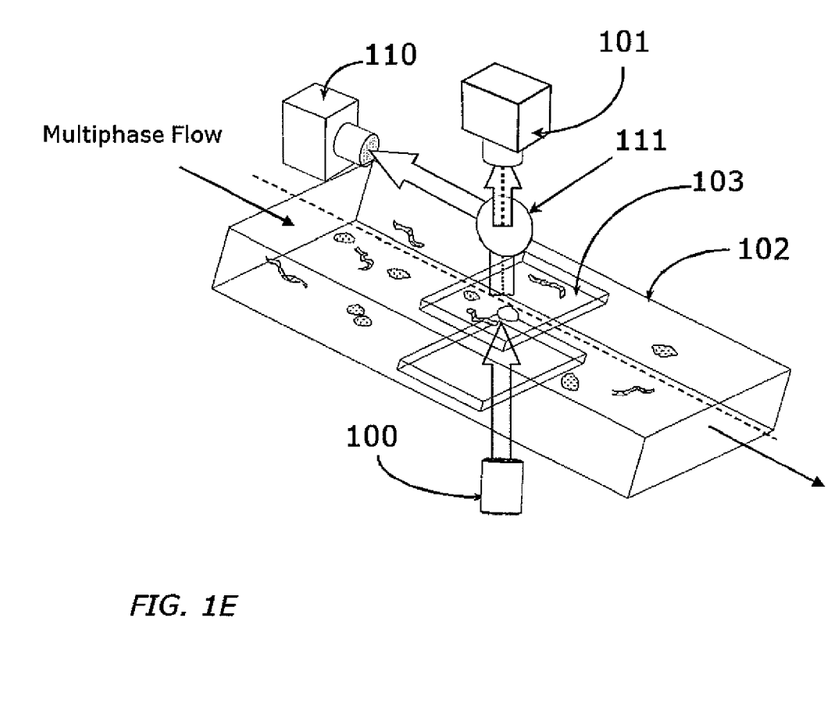
FIG. 1E is a perspective view of a fourth embodiment of the invention.

A second aspect of the invention uses a combination of cameras to monitor both fluorescence from hydrophobic particles coated with a fluorophore dye and transmittance properties through the multiphase fluid to identify hydrophilic particles, fibers, and flocculants. An illustration of the dual camera system is shown in FIG. 1E with camera 101 monitoring the fluorescence of hydrophobic particles and camera 102 monitoring the overall transmission characteristics through the multiphase fluid. The illumination and excitation source is directed through the fluid and then split using a dichoric element 111 that allows transmission of the emission light and reflects the excitation light. Camera 110 monitors the excitation light that will be attenuated by the fiber, floc, and particle density in the fluid. By simultaneously collecting and processing images from cameras 101 and 110 allows identification of hydrophilic and hydrophobic particles as well as fibers with and without hydrophobic material absorbed on to the surface. A combination using reflectance for hydrophobic particle detection and transmission through the fluid for overall fiber and particle monitoring is an alternative configuration. In this case the dichroic element 111 is still used as a filter and reflecting element. A variation of the configuration shown in FIG. 1E involves using a beam splitting prism (not shown) with the dual cameras. Simultaneous monitoring of different fluid characteristics can be made with proper filtering known in the art. Additionally, a multiple camera system can also be used to monitor at different optical depths in the fluid.

Figures 1F, 1G:
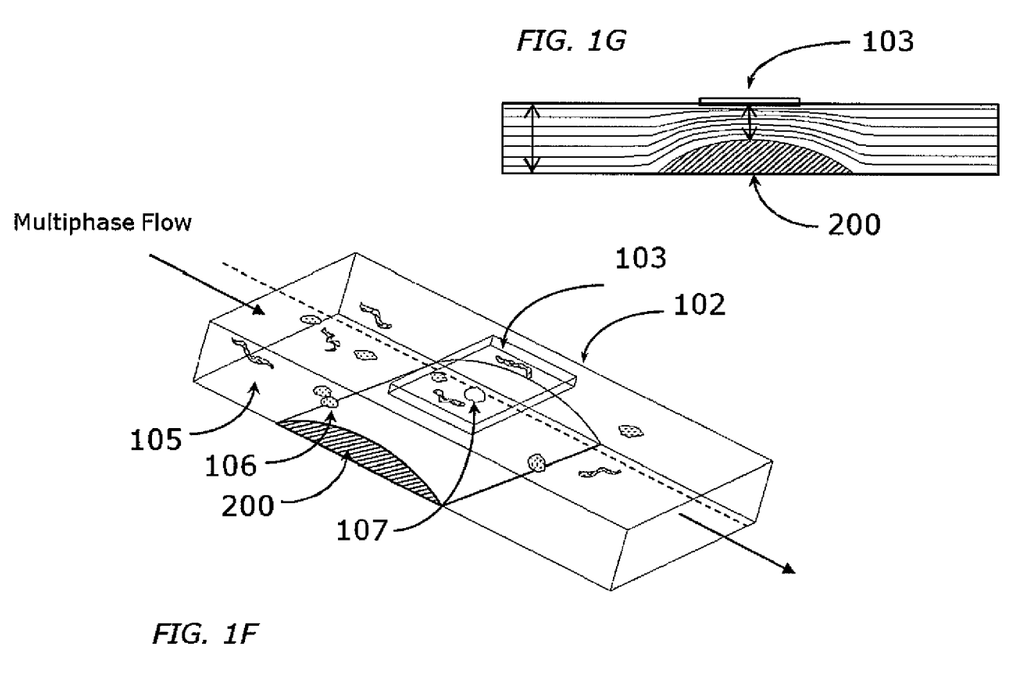
FIG. 1F is a perspective view of a fifth embodiment of the invention, which includes a streamlined body.
FIG. 1G is a side view of a fifth embodiment of the invention, which also includes a streamlined body.

A third aspect of the invention is a method to concentrate the multiphase fluid in the measurement area by using a streamlined body 200 as shown in FIGS. 1F and 1G. By inserting the streamlined body 200 in the flow, the area near the measurement zone is reduced thereby concentrating the solid material closer to the focal plane of the imaging system. The geometry of the streamlined body 200 provides a smooth transition as the fluid approaches and flows around the body provided the Reynolds number for the flow remains below the turbulent transition level ($Re_D<4000$). Use of the streamlined body will enhance detection by increasing the number of particles flowing through the focal plane of the imaging system. Additionally, the design minimizes the pressure drop through the flow cell as well as reducing the risk of plugging.

A fourth aspect of the invention is based on capturing sticky particles (micro and macro) on an optical window coated with a semi hydrophobic transparent material similar to that described by Shevchenko et al. (U.S. Patent Application Publication No. 2009/0056897) and its continuation-in-part (U.S. patent application Ser. No. 12/907,478, filed in Oct. 19, 2010), both applications herein incorporated by reference. However, instead of using a quartz crystal microbalance to detect the accumulation of sticky particles adhering to a coated substrate, here the method is based on monitoring the change in fluorescence over time. The configuration is similar to FIG. 1A, but the optical access window 103 is coated with a hydrophobic material. Particles adhering to the window are detected by fluorescence using the excitation source 100. In this case, the flow dynamics are removed from the measurement, thus reducing the imaging requirements (exposure time, quantum efficiency, capture rate, etc.). As the number of particles buildup on the surface, the intensity and/or area covered will change in time. Trending this data over time will show the rate of stickies accumulation on the coated window. Change in the rate of accumulation can be related to the effect and concentration of chemical additives, furnish composition, or process operational changes.

Finally, all the configurations shown in FIGS. 1A, 1C, 1D, and 1E can be used with streamlined body 200. In the case where light is transmitted opposite the camera (through the cell bottom as shown in FIGS. 1D and 1E), the streamlined body 200 can be optically transparent. If designed properly an optically transparent streamlined body can act as collimating lines for light introduced through the cell bottom.

An embodiment of the present invention is a method for monitoring the size of at least one macroscopic contaminant, or the concentration of macroscopic contaminants, in an aqueous medium, such as an aqueous pulp slurry, and more particularly aqueous recycled pulp slurry. The aqueous medium is comprised of contaminants, both macroscopic and microscopic. The method comprises the steps of providing a flow of the aqueous pulp slurry; injecting a hydrophobic dye into the flow of the aqueous pulp slurry, the injecting performed so that the hydrophobic dye interacts with the contaminants, the interaction causing a change in fluorescent emission; capturing an image of the change in fluorescent emission, the image having a background; correcting the background of the image; filtering from the image the captured change in fluorescent emission caused by the non-macroscopic contaminant; and quantifying the particle size of the at least one macroscopic contaminant, or the concentration of the macroscopic contaminants, using the non-filtered captured change in fluorescent emission. The method is performed with an apparatus comprising a flow-through cell, a light source, and at least one digital microscopic camera. The correcting the background strengthens the captured change in fluorescent emission caused by the interaction of the hydrophobic dye and the macroscopic contaminant(s), while it weakens the captured change in fluorescent emission of the non-macroscopic contaminant(s) and fibers coated with a hydrophobic layer. The emission from the fibers is much less intense than from the visible/macroscopic hydrophobic contaminants.

In another embodiment, the invention is a method for measuring the effectiveness of an additive. The additive is added to an aqueous slurry to decrease deposition of macroscopic contaminants in a papermaking process. The aqueous slurry is comprised of contaminants, both macroscopic and microscopic. The method comprises the steps of providing a flow of the aqueous slurry; injecting a hydrophobic dye into the flow of the aqueous slurry, the injecting performed so that the hydrophobic dye interacts with the contaminants, the interaction causing a first change in fluorescent emission; capturing an image of the first change in fluorescent emission, the image having a background; correcting the background of the image; filtering from the image the captured first change in fluorescent emission caused by the non-macroscopic contaminant; adding an additive to the aqueous slurry; repeating the injecting, the capturing, the correcting, and the filtering steps to create a non-filtered captured second change in fluorescent emission; and comparing the non-filtered captured second change in fluorescent emission with the non-filtered captured first change in fluorescent emission. The method is performed with an apparatus comprising a flow-through cell, a light source, and at least one digital microscopic camera. The correcting the background strengthens the captured changes in fluorescent emission caused by the interaction of the hydrophobic dye and the macroscopic contaminants, while it weakens the captured changes in fluorescent emission of the non-macroscopic contaminants.

In yet another embodiment, the invention is a method for measuring the effectiveness of a microstickies fixative additive that decreases the concentration of non-visible (colloidal) microstickies in an aqueous slurry. The fixative additive attaches evenly to the surface of a fiber. As a result, the fluorescence of hydrophobically-coated fiber increases. The increase can be used to quantify the effect of the fixative. Typically, the fiber fluorescence is filtered as background from the captured image. In this embodiment, the filter is set up in such a way that the coated fiber fluorescence is measured and the fluorescence corresponding with both the visible and colloidal contaminants is filtered from the captured image.

The additive is added to the aqueous slurry to decrease deposition of hydrophobic macroscopic contaminants in a papermaking process. The aqueous slurry is typically comprised of hydrophobic contaminants, both macroscopic and microscopic. The method comprises the steps of providing a flow of the aqueous slurry; injecting a hydrophobic dye into the flow of the aqueous slurry, the injecting performed so that the hydrophobic dye interacts with the contaminants, the interaction causing a change in fluorescent emission; capturing an image of the change in fluorescent emission, the image having a background; correcting the background of the image; filtering from the image the captured change in fluorescent emission caused by the macroscopic and microscopic free-floating contaminants; and determining the effectiveness of the additive using the non-filtered captured change in fluorescent emission caused by the fiber. The determining step may be performed by comparing the measured change in fluorescent emission caused by the fiber to average values or by any other means available to one skilled in the art. The method is performed with an apparatus comprising a flow-through cell, a light source, and at least one digital microscopic camera. The correcting the background strengthens the captured change in fluorescent emission caused by the interaction of the hydrophobic dye and the hydrophobic layer on the surface of the fibers, while it weakens the captured change in fluorescent emission of the free-floating contaminants.

In trying to prevent contaminants from depositing onto papermaking equipment, one may add a chemical to an aqueous slurry. The effectiveness of the additive may be measured via the invention by determining whether the concentration of macroscopic contaminants has increased, decreased, remained unchanged, falls within a selected range, or the particle size of the contaminants has become larger, smaller, or remained the same. The effectiveness of one specific class of additives that may include fixative additives can also be measured based on the change in fluorescence of hydrophobically-coated fibers that increases when more contaminants are fixed onto the fibers. Such a measurement could allow for the comparison of the effectiveness of one additive with another (or several), or the measurement could allow for optimization of the quantity or concentration of the additive to the aqueous pulp slurry. Similar calculations or comparisons could be performed for pulp sources, process variables, or any place where one of skill in the art may see fit.

The light source may take the form of an LED, which is a preferred embodiment.

The hydrophobic dye may be a solvatochromatic dye, such as a chemical comprising a phenoxazone dye, a carbocyanine, a pyridinium betaine dye, a polysulfonated pyrene, a rhodamine, a fluorescein, or some combination of one or more of these chemicals. A particularly preferred embodiment of the hydrophobic dye is comprised of Nile Red.

The hydrophobic dye may be dissolved in an organic solvent that is miscible in water, such as methanol, ethanol, propanol, isopropanol, butanol, or some combination of one or more of these solvents.

Figure 2:
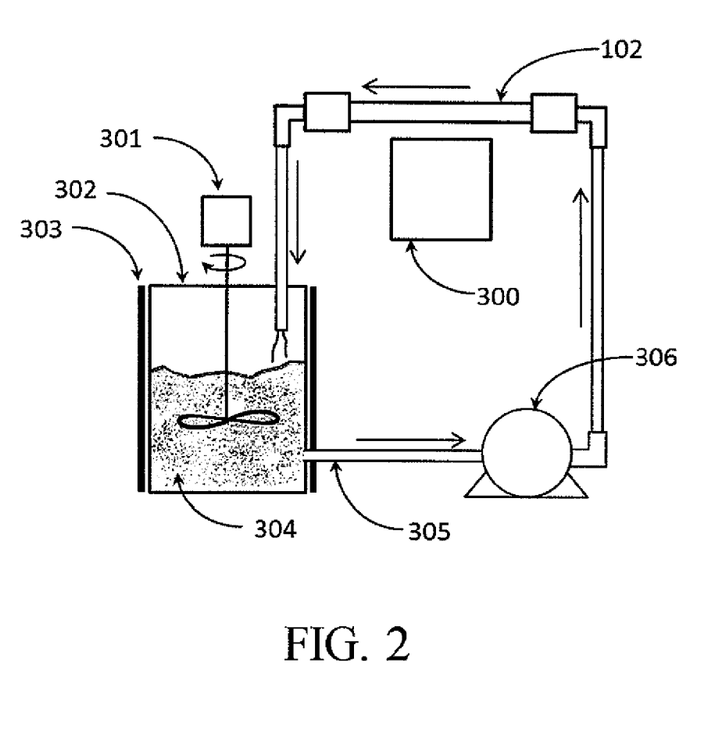
FIG. 2 is a schematic of an embodiment of the hydrophobic batch analysis apparatus.

Illustrated in FIG. 2 is an embodiment of a hydrophobic batch analysis system. For conducting an analysis, pulp slurry 304 is held in a container 302. A heating element 303 wraps around container 302 for sample heating and to maintain temperature. Mixer 301 is used to ensure that the pulp is evenly distributed in the aqueous solution, as well as to provide rapid mixing between the slurry and the added dye solution. As illustrated, flow of the mixer (pulp slurry and dye) circulates counter clockwise by exiting container 302 through tube 305 and pumped through sample cell 102, as previously described, using pump 306. Analysis of the flowing slurry is made using imaging system 300 that consists of an imaging device and excitation source, as previously described. After the sample cell the slurry is returned back to container 302.

In an embodiment, the variable is a particle size distribution.

In an embodiment, the variable is a concentration.

In an embodiment, the variable is a particle count.

In an embodiment, the variable is an effectiveness of an additive.

The flow of the aqueous slurry can be provided from a processing stage of a papermaking process. Such a stage may be a repulping stage, a deinking stage, a water loop stage, a wet-end stock preparation stage, a papermaking stage, or a tissue-making stage. One of skill in the art would readily identify these stages and each's corresponding unit operations. The flow of the aqueous slurry can be provided from either a closed-loop circulation system, where the flow is supported by a pump, or from a sidestream arrangement at a mill.

Examples

A portable batch analyzer as illustrated in FIG. 2, using a flow cell and optical imaging system, was tested on a continuous pulp flow in a closed-loop circulation system. The analyzer included a bucket mixer mixing at 400 rpm, a flow rate of 1.2 gpm, a pulp pre-heater when needed, and the temperature maintained by a heated external blanket and a thermocouple. The optical system could be used as a benchtop instrument or reconfigured for continuous on-line monitoring. For these examples, a benchtop setup was used. Fresh pulp was sampled from a first source. The fresh pulp was made from recycled fiber and then diluted 1:4 with water, to 15 L. Nile red dye was added to the diluted slurry, 30 mL of 0.1% weight dye solution in isopropanol under mixing and the recording started immediately (except for the experiment documented in Table II). The data obtained were electronically stored. Using the proper camera and imaging processing settings listed in Table I below, the fluorescing stickies could be detected in the diluted pulp flow with no interference from pulp fibers. Fluorescence from fibers was present, as expected, but much weaker than the emission from the particles. Considering that every test took 11 min, the timing was set in the middle of the test for the experiments documented in Tables IV-VI.

TABLE I

Camera configuration and processing settings for data collected in Tables II-VI.

Camera Configuration

| | |
|---|---|
| Camera: | Imaging Source DMK 31BU03 |
| Exposure: | 300 microseconds (1/3333) |
| Gain: | 900 |
| Frame Rate: | 7.5/second |
| Lens: | Pentax 25 mm f/1.4 with 10 mm extension tube |
| Filter: | Newport 5CGA-590 band pass filter |
| Calibration: | 10.05 micron/pixel |
| Frame number: | 5000 (11 min per test) |
| Iteration time: | 100 |

Image Processing Conditions

| Processing Step | |
|---|---|
| 1 | Power Function: 2.66 |
| 2 | Threshold Setting: Lower Level = 20, Upper Level = 255 |
| 3 | Particle Filter (reject <80 micron dia.) |
| 4 | Store Particle Size Data |

In order to have comparable data, the dilution and consistency of each pulp needed to be factored into the data. The number of particles adjusted for consistency, indicated as No. adj. cons./100 in the tables below, represents comparable values between the two pulps. The values were calculated by dividing the number of particles by the dilution ratio (20%), then dividing by the consistency. The "No. adj. cons." were then arbitrarily divided by 100, and those values are reported in the tables below.

For the first experiment, a pulp having a low stickies content was used. The pulp had a consistency of 1.68%. In this experiment, the data were collected seven times starting after 45 mins. since the dye was added in order to provide full saturation beyond an induction period. The data show good reproducibility in both number of particles and particle size distribution. Table II illustrates the results of the first experiment.

For the second experiment, a more contaminated pulp was characterized in the same manner. The pulp had a consistency of 4.15%. In this experiment, the data were collected continuously right after the dye was added. This test provided a dynamic picture and demonstrated the length of induction period before full saturation (40 mins. at room temperature; time to full saturation was reduced dramatically by adjusting the temperature to standard repulping conditions of 40° C.). The data show good reproducibility in both number of particles and particle size distribution upon the achievement of saturation. Table III illustrates the results of the second experiment. Comparison of the two experiments demonstrated consistent data for the two samples, gave an example of an induction period before dye equilibration, and allowed comparing contamination of the two pulps that matched the expectations. The ratio of stickies content approximately equaled 1:6.5, which was the expected ratio.

In this third experiment, we varied testing temperature to assess its effect on the time of saturation. Under the chosen conditions, at room temperature stable readings (saturation) are achieved in about 1 hr. Increasing the temperature to 40° C. shortens this time to about 30 min and further increasing temperature to 55° C. (at the moment of adding the dye) to approximately 15 min.

TABLE II

Results for the First Experiment (Pulp with Low Stickies Content)

| Number | No. of Particles | Range | Mean | Std. Dev. | No. adj. cons./100 |
|---|---|---|---|---|---|
| 1 | 85 | 3748 | 394 | 427 | 252.9762 |
| 2 | 66 | 4006 | 292 | 498 | 196.4286 |
| 3 | 65 | 3812 | 372 | 530 | 193.4524 |
| 4 | 62 | 3410 | 369 | 484 | 184.5238 |
| 5 | 57 | 2295 | 363 | 378 | 169.6429 |
| 6 | 79 | 1328 | 296 | 233 | 235.1190 |
| 7 | 60 | 1218 | 279 | 206 | 178.5714 |
| | | | | AVG: | 204.3651 |

TABLE III

Results for the Second Experiment (Pulp with High Stickies Content)

| Number | Time, min. | No. of Particles | Range | Mean | Std. Dev. | No. adj. cons./100 |
|---|---|---|---|---|---|---|
| 0 | 0 | 14 | 188 | 199 | | |
| 1 | 3 | 140 | | | | 168.6747 |
| 2 | 6 | 538 | 309 | 187 | 85 | 648.1928 |
| 3 | 18 | 811 | 506 | 201 | 93 | 977.1084 |
| 4 | 30 | 956 | 579 | 204 | 94 | 1151.807 |
| 5 | 42 | 1116 | 696 | 209 | 103 | 1344.578 |
| 6 | 54 | 1079 | 605 | 209 | 00 | 1300.000 |
| 7 | 66 | 1128 | 804 | 204 | 97 | 1359.036 |
| | | | | | Nos. 5-7 AVG: | 1334.538 |

TABLE IV

Results for the experiment conducted at 25° C.

| Number | Time, min. | No. of Particles | Range | Mean | Std. Dev. | No. adj. cons./100 |
|---|---|---|---|---|---|---|
| 1 | 6 | 6 | 376 | 355 | 152 | 18 |
| 2 | 16.5 | 19 | 537 | 257 | 164 | 57 |
| 3 | 29 | 34 | 554 | 214 | 123 | 101 |
| 4 | 40.5 | 35 | 376 | 203 | 107 | 104 |
| 5 | 53 | 44 | 569 | 242 | 143 | 131 |
| 6 | 86 | 63 | 599 | 276 | 167 | 187 |
| 7 | 98 | 68 | 613 | 253 | 132 | 202 |
| 8 | 153 | 61 | 842 | 314 | 181 | 182 |
| 9 | 165 | 55 | 1190 | 320 | 206 | 164 |
| 10 | 206.5 | 60 | 544 | 236 | 137 | 179 |
| | | | | | Av. 6-10 | 187 |

TABLE V

Results for the experiment conducted at 40° C.

| Number | Time, min. | No. of Particles | Range | Mean | Std. Dev. | No. adj. cons./100 |
|---|---|---|---|---|---|---|
| 1 | 6 | 11 | 514 | 268 | 158 | 33 |
| 2 | 19.5 | 41 | 539 | 285 | 164 | 122 |
| 3 | 31.5 | 52 | 696 | 275 | 169 | 155 |
| 4 | 45.5 | 56 | 753 | 276 | 169 | 167 |
| 5 | 75.5 | 58 | 799 | 304 | 205 | 173 |
| 6 | 133.5 | 46 | 773 | 284 | 160 | 137 |
| 7 | 145.5 | 58 | 800 | 310 | 198 | 173 |
| | | | | | Av. 3-7 | 159 |

TABLE VI

Results for the experiment conducted at 55° C.

| Number | Time, min. | No. of Particles | Range | Mean | Std. Dev. | No. adj. cons./100 |
|---|---|---|---|---|---|---|
| 1 | 6 | 17 | 527 | 263 | 153 | 51 |
| 2 | 17.5 | 63 | 575 | 252 | 157 | 187 |
| 3 | 29.5 | 63 | 1006 | 245 | 170 | 187 |
| 4 | 175.5 | 54 | 704 | 282 | 176 | 161 |
| 5 | 186.5 | 69 | 778 | 296 | 181 | 205 |
| 6 | 198.5 | 65 | 572 | 274 | 157 | 193 |
| | | | | | Av. 2-6 | 187 |

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the illustrated specific embodiments or examples is intended or should be inferred. The disclosure is intended to cover by the appended claims all such modifications as fall within the scope of the claims.

We claim:

1. A method for measuring the effectiveness of an additive added to an aqueous pulp slurry for decreasing macrostickie contaminants, the method comprising:
    shining light into an aqueous pulp slurry comprising macrostickie and non-macrostickie contaminants flowing across a streamlined body;
    adding a hydrophobic dye to the aqueous pulp slurry, such that the hydrophobic dye interacts with the macrostickie and non-macrostickie contaminants, the interaction causing a first modified fluorescent emission;
    capturing a digital image of the first modified fluorescent emission, the digital image having a background;
    correcting the background of the digital image;
    filtering from the digital image the first modified fluorescent emission caused by the non-macrostickie contaminant to create a first filtered image;
    adding an additive to the aqueous pulp slurry;
    repeating the shining, adding, detecting, capturing, correcting, and filtering to create a second filtered image; and
    comparing the first filtered image to the second filtered image to determine the effectiveness of the additive;
    wherein the streamlined body narrows the flow of the aqueous pulp slurry in the measurement area.

2. The method of claim 1, further comprising measuring a variable of the aqueous pulp slurry based on the altered digital image, wherein the variable is selected from a particle size distribution of macrostickies in the aqueous pulp slurry and a concentration of macrostickies in the aqueous pulp, and combinations thereof.

3. The method of claim 1, wherein the hydrophobic dye is a solvatochromatic dye comprised of a chemical selected from the group consisting of a phenoxazone dye, a carbocyanine, a pyridinium betaine dye, a polysulfonated pyrene, a rhodamine, a fluorescein, and combinations thereof.

4. The method of claim 1, wherein the hydrophobic dye is Nile Red.

5. The method of claim 1, wherein the hydrophobic dye is dissolved in a solvent that is miscible in water.

6. The method of claim 1, wherein the aqueous pulp slurry originates from a processing stage selected from the group consisting of a repulping stage, a deinking stage, a water loop stage, a wet-end stock preparation stage, a papermaking stage, and a tissuemaking stage.

7. The method of claim 1, wherein capturing a digital image of the modified fluorescent emission further includes capturing a digital image of modified fluorescent emission due to the presence in the slurry of contaminant other than macrostickies, and altering the digital image comprising strengthening the captured modified fluorescent emission due to the presence of macrostickies, and weakening the captured modified fluorescent emission due to the presence of contaminant other than macrostickies.

8. The method of claim 7, wherein altering the digital image further comprises filtering the digital image to remove weakened modified fluorescent emission and measuring the strengthened captured modified fluorescent emission.

9. The method of claim 7, wherein at least the capturing, the altering, and the measuring are repeated.

10. The method of claim 1, wherein the capturing is performed at a flow-through cell having an optical access window coated with a hydrophobic material.

11. A method of monitoring a variable, the method comprising;
shining light into an aqueous pulp slurry having visible contaminants flowing across a streamlined body;
adding a hydrophobic dye into the aqueous pulp slurry such that a modified fluorescent emission occurs and is capturable in the flow across the streamlined body;
capturing, via a digital camera, a digital image of the modified fluorescent emission in the aqueous pulp slurry flowing across the streamlined body;
altering the digital image to isolate the fluorescent emission caused by the interaction of the hydrophobic dye with at least one visible contaminant of the visible contaminants;
and measuring the variable of the aqueous pulp slurry based on the altered digital image;
wherein the streamlined body narrows the flow of the aqueous pulp slurry in the measurement area;
wherein the variable is selected from concentration of the visible contaminants, average particle size of the visible contaminants, effectiveness of an additive added to the aqueous pulp slurry, and combinations thereof.

12. The method of claim 11, wherein the hydrophobic dye is a solvatochromatic dye comprised of a chemical selected from a phenoxazone dye, a carbocyanine, a pyridinium betaine dye, a polysulfonated pyrene, a rhodamine, a fluorescein, and combinations thereof.

13. The method of claim 11, wherein the hydrophobic dye is Nile Red.

14. The method of claim 11, wherein the altering comprises correcting the digital image, the correcting strengthening the captured modified fluorescent emission caused by the interaction of the hydrophobic dye and the visible contaminant, and weakening the captured modified fluorescent emission caused by the interaction of the hydrophobic dye and anything other than the visible contaminant.

15. The method of claim 1, wherein one or more of the macrostickie contaminants have a particle size of 100 microns or more.

16. The method of claim 11, wherein one or more of the macrostickie contaminants have a particle size of 100 microns or more.

17. The method of claim 11, wherein the aqueous pulp slurry originates from a processing stage selected from the group consisting of a repulping stage, a deinking stage, a water loop stage, a wet-end stock preparation stage, a papermaking stage, and a tissuemaking stage.

18. The method of claim 11, wherein at least the capturing, the altering, and the measuring are repeated.

19. The method of claim 11, wherein the variable is the concentration of the visible contaminants.

20. The method of claim 1, wherein the light is from a LED light source.

21. The method of claim 11, wherein the light is from a LED light source.

* * * * *